US010825992B2

(12) United States Patent
Bascour et al.

(10) Patent No.: US 10,825,992 B2
(45) Date of Patent: *Nov. 3, 2020

(54) SPIROBIFLUORENE COMPOUNDS FOR LIGHT EMITTING DEVICES

(71) Applicant: Sumitomo Chemical Company, Limited, Tokyo (JP)

(72) Inventors: Dominique Bascour, Grez-Doiceau (BE); Jonathan Maunoury, Brussels (BE); Enrico Orselli, Brussels (BE)

(73) Assignee: SUMITOMO CHEMICAL CO., LTD, Tokyo (JP)

( * ) Notice: Subject to any disclaimer, the term of this patent is extended or adjusted under 35 U.S.C. 154(b) by 446 days.

This patent is subject to a terminal disclaimer.

(21) Appl. No.: 14/347,661

(22) PCT Filed: Sep. 24, 2012

(86) PCT No.: PCT/EP2012/068809
§ 371 (c)(1),
(2) Date: Mar. 27, 2014

(87) PCT Pub. No.: WO2013/045411
PCT Pub. Date: Apr. 4, 2013

(65) Prior Publication Data
US 2014/0231713 A1    Aug. 21, 2014

(30) Foreign Application Priority Data

Sep. 28, 2011 (EP) .................................... 11007868
Aug. 22, 2012 (EP) .................................... 12005988

(51) Int. Cl.
*H01L 51/50* (2006.01)
*H01L 51/00* (2006.01)
*C07D 265/38* (2006.01)

(52) U.S. Cl.
CPC ........ *H01L 51/0056* (2013.01); *C07D 265/38* (2013.01); *H01L 51/0067* (2013.01); *H01L 51/0071* (2013.01); *H01L 51/0072* (2013.01)

(58) Field of Classification Search
CPC ............. H01L 51/0055; H01L 51/0056; H01L 51/0067; H01L 51/0071; H01L 51/0072; H01L 51/50; H01L 51/5012; H01L 51/5016; C09K 11/06; C09K 2211/1011; C09K 2211/1029; C09K 2211/1044; C09K 2211/1059; C09K 2211/1074; C07D 265/38; C07D 219/02; C07C 13/54; C07C 13/547; C07C 13/567; C07C 13/72; C07C 2103/94
USPC ................... 428/690, 691, 917; 427/58, 66; 313/500–512; 257/40, 88–104, 257/E51.001–E51.052; 252/301.16–301.35; 546/102; 585/26
See application file for complete search history.

(56) References Cited

U.S. PATENT DOCUMENTS

| 5,374,489 A | 12/1994 | Imai et al. |
| 5,891,587 A * | 4/1999 | Hu ...................... H01L 51/5012 313/503 |
| 6,242,115 B1 * | 6/2001 | Thomson .............. C07C 211/54 257/94 |
| 6,335,480 B1 | 1/2002 | Bach et al. |
| 6,664,071 B1 | 12/2003 | Windhab et al. |
| 6,893,743 B2 | 5/2005 | Sato et al. |
| 7,714,145 B2 | 5/2010 | Tsai et al. |
| 2002/0125818 A1 | 9/2002 | Sato et al. |
| 2002/0182439 A1 | 12/2002 | Tao et al. |
| 2003/0111107 A1 | 6/2003 | Salbeck et al. |
| 2003/0157366 A1 * | 8/2003 | Matsuura ............... C09K 11/06 428/690 |
| 2006/0141287 A1 | 6/2006 | Klubek et al. |
| 2007/0003785 A1 | 1/2007 | Slusarek et al. |
| 2007/0215867 A1 | 9/2007 | Kawakami et al. |
| 2007/0240761 A1 | 10/2007 | Miteva et al. |
| 2009/0066226 A1 * | 3/2009 | Sugita .................. C07D 405/14 313/504 |
| 2009/0167166 A1 | 7/2009 | Bach et al. |
| 2009/0220706 A1 * | 9/2009 | Yamazaki ............... C23C 14/28 427/596 |
| 2009/0273278 A1 * | 11/2009 | Lee ......................... C07C 15/20 313/504 |
| 2009/0302758 A1 | 12/2009 | Saitoh et al. |
| 2010/0019657 A1 | 1/2010 | Eum et al. |
| 2010/0171417 A1 * | 7/2010 | Kitamura ............. C07D 401/10 313/504 |
| 2010/0240856 A1 | 9/2010 | Veinot et al. |
| 2010/0289006 A1 | 11/2010 | Chen et al. |
| 2011/0037027 A1 * | 2/2011 | Stoessel ................ C07C 13/567 252/301.16 |

(Continued)

FOREIGN PATENT DOCUMENTS

| CN | 101508649 A | 8/2009 |
| EP | 2312667 A1 | 4/2011 |

(Continued)

OTHER PUBLICATIONS

Nomura et al., machine translation of JP 2011-082507 A, date of Japanese language publication Apr. 2011, pp. 1-114.*
Enokida et al., machine translation of JP 2002-265938, 2002, pp. 1-41. (Year: 2002).*
Hartmann et al., Machine Translation of WO-2007110228-A1 (2007) pp. 1-9. (Year: 2007).*

(Continued)

*Primary Examiner* — Dylan C Kershner

(74) *Attorney, Agent, or Firm* — Panitch Schwarze Belisario & Nadel LLP

(57) ABSTRACT

Novel spirobifluorene compounds for light emitting devices where the spirobifluorene ring system comprises at least one acridine-type substituent.

9 Claims, 1 Drawing Sheet

(56) References Cited

U.S. PATENT DOCUMENTS

| | | | |
|---|---|---|---|
| 2011/0084254 A1 | 4/2011 | Kim et al. | |
| 2011/0127503 A1 | 6/2011 | Takahashi et al. | |
| 2011/0309341 A1* | 12/2011 | Ohuchi | C08G 61/02 257/40 |
| 2012/0228552 A1* | 9/2012 | Parham | C07D 403/10 252/301.16 |
| 2013/0207046 A1 | 8/2013 | Pflumm et al. | |
| 2014/0138670 A1 | 5/2014 | Nakagawa et al. | |
| 2014/0158859 A1 | 6/2014 | Fukuzaki et al. | |
| 2014/0203216 A1 | 7/2014 | Parham et al. | |
| 2014/0231713 A1 | 8/2014 | Bascour et al. | |
| 2014/0326979 A1* | 11/2014 | Bascour | C07D 265/38 257/40 |

FOREIGN PATENT DOCUMENTS

| | | | | |
|---|---|---|---|---|
| JP | 2002231453 A | | 8/2002 | |
| JP | 2002265938 A | * | 9/2002 | |
| JP | 2003077674 A | | 3/2003 | |
| JP | 2005085599 A | | 3/2005 | |
| JP | 2006089585 A | | 4/2006 | |
| JP | 2006131782 A | | 5/2006 | |
| JP | 2009170813 A | | 7/2009 | |
| JP | 2009215281 A | | 9/2009 | |
| JP | 2009538841 A | | 11/2009 | |
| JP | 2010027681 A | * | 2/2010 | |
| JP | 2010027681 A | | 2/2010 | |
| JP | 2010150518 A | | 7/2010 | |
| JP | 4581355 B2 | | 11/2010 | |
| JP | 2010272618 A | | 12/2010 | |
| JP | 2011082507 A | * | 4/2011 | |
| JP | 2011521894 A | | 7/2011 | |
| JP | 2011173973 A | | 9/2011 | |
| JP | 2012227015 A | | 11/2012 | |
| JP | 2013041995 A | | 2/2013 | |
| JP | 2013253121 A | | 12/2013 | |
| JP | 2014534161 A | | 12/2014 | |
| JP | 2014534950 A | | 12/2014 | |
| JP | 2015500793 A | | 1/2015 | |
| KR | 20090018503 A | | 2/2009 | |
| KR | 20100006072 A | * | 1/2010 | |
| KR | 20100006072 A | | 1/2010 | |
| KR | 20100082049 A | | 7/2010 | |
| KR | 101029082 B1 | | 4/2011 | |
| TW | 554029 B | | 9/2003 | |
| TW | 200846442 A | | 12/2008 | |
| TW | 201229007 A | | 7/2012 | |
| TW | 201309696 A | | 3/2013 | |
| TW | 201311612 A | | 3/2013 | |
| WO | 2004058912 A2 | | 7/2004 | |
| WO | WO-2007110228 A1 | * | 10/2007 | C07D 219/02 |
| WO | 2010050781 A1 | | 5/2010 | |
| WO | 2010058859 A1 | | 5/2010 | |
| WO | WO-2010050781 A1 | * | 5/2010 | C07D 401/04 |
| WO | WO-2010058859 A1 | * | 5/2010 | C08G 61/02 |
| WO | 2011006574 A1 | | 1/2011 | |
| WO | 2011049325 A2 | | 4/2011 | |
| WO | WO-2011049325 A2 | * | 4/2011 | C09K 11/06 |
| WO | WO-2011060877 A2 | * | 5/2011 | C07D 403/10 |
| WO | 2012034627 A1 | | 3/2012 | |
| WO | 2012048820 A1 | | 4/2012 | |
| WO | 2012085983 A1 | | 6/2012 | |
| WO | 2013011955 A1 | | 1/2013 | |
| WO | 2013011956 A1 | | 1/2013 | |
| WO | 2013017192 A1 | | 2/2013 | |
| WO | 2013045408 A1 | | 4/2013 | |
| WO | 2013045410 A1 | | 4/2013 | |
| WO | 2013045411 A1 | | 4/2013 | |

OTHER PUBLICATIONS

Tsuzuki et al., Machine Translation of JP-2010027681-A (2010) pp. 1-14. (Year: 2010).*
Ahn, Jun Su, machine translation of KR-20100006072-A (2010), pp. 1-173. (Year: 2010).*
Salbeck. et. al—Spiro Compounds for Organic Optoelectronics; Chem. Rev., 2007, 107 (4), pp. 1011-1065.
Office Action dated Jul. 28, 2017 in U.S. Appl. No. 14/347,665 by Bascour.
Office Action dated Feb. 25, 2015 in CN Application No. 201280058424.2.
Office Action dated Nov. 4, 2015 in CN Application No. 201280058424.2.
Office Action dated Jul. 8, 2016 in CN Application No. 201280058424.2.
Office Action dated Jun. 24, 2015 in EP Application No. 12766066.0.
Salbeck et al, "Spiro Compounds for Organic Optoelectronics," Chem.Rev, vol. 107, pp. 1011-1065 (2007).
Int'l Search Report and Written Opinion dated Nov. 20, 2012 in Int'l Application No. PCT/EP2012/068809.
Extended Search Report dated May 4, 2012 in EP Application No. 11007868.0.
Office Action dated May 30, 2016 in JP Application No. 2014-532340.
Office Action dated Feb. 17, 2016 in TW Application No. 101134961.
Office Action dated Jun. 30, 2015 in CN Application No. 201280058419.1.
Office Action dated Jan. 21, 2016 in CN Application No. 201280058419.1.
Office Action dated Sep. 23, 2016 in CN Application No. 201280058419.1.
Office Action dated Jan. 31, 2017 in JP Application No. 2014-532339.
Office Action dated Dec. 19, 2016 in EP Application No. 12769363.8.
Office Action dated Feb. 7, 2017 in CN Application No. 201280058496.7.
Office Action dated Jan. 31, 2017 in JP Application No. 2014-532340.
Office Action dated Mar. 14, 2016 in CN Application No. 201280058496.7.
Zhuang et al, "Polyfluorene-Based—Pull Type Functional Materials for Write-Once-Read-Many-Times Memory Devices," Chemistry of Materials, vol. 22, No. 15, pp. 4455-4461 (Jul. 16, 2010).
Office Action dated Jul. 4, 2016 in EP Application No. 12766430.8.
Int'l Search Report and Written Opinion dated Dec. 10, 2012 in Int'l Application No. PCT/EP2012/068805.
Extended Seach Report dated Dec. 6, 2011 in EP Application No. 11007867.2.
El-Khouly et al, "Photoinduced Intermolecular Electron Transfer Process of Fullerene (C60) and Amine-Substituted Fluorenes Studied by Laser Flash Photolysis," Spectrochimica Acta. Part A: Molecular and Biomolecular Spectroscopy, vol. 67, pp. 636-642 (Jul. 1, 2007).
Kuhl et al, "Nickel(O)/N-Heterocyclic Carbene Complexes Catalysed Arylation of Aromatic Diamines," Journal of Organometallic Chemistry, vol. 690, No. 24-25, pp. 6169-6177 (Dec. 1, 2005).
Fournier et al, "Molecular Tectonics Porous Hydrogen-Bonded Networks Built from Derivatives of 9,9'—Spirobifluorene," Journal of Organic Chemistry, vol. 69, No. 6, pp. 1762-1775 (Sep. 13, 2003).
Office Action dated Jan. 4, 2016 in JP Application No. 2014-532338.
Office Action dated Jan. 21, 2016 in TW Application No. 101134958.
Office Action dated Nov. 24, 2016 in TW Application No. 101134958.
Office Action dated Feb. 25, 2015 in CN Application No. 201280058419.
Office Action dated Mar. 3, 2017 in CN Application No. 201280058424.
Office Action dated Oct. 21, 2016 in U.S. Appl. No. 14/347,665, by Bascour.
Office Action dated Oct. 19, 2016 in U.S. Appl. No. 14/347,666, by Bascour.
Office Action dated Jul. 19, 2017 in U.S. Appl. No. 14/347,666, by Bascour.
Office Action dated May 30, 2016 in JP Application No. 2014-532339 (English translation only).
Office Action dated Jan. 18, 2016 in EP Application No. 12769363.

(56) References Cited

OTHER PUBLICATIONS

Int'l Search Report and Written Opinion dated Feb. 14, 2013 in Int'l Application No. PCT/EP2012/068807.
Office Action dated Jan. 13, 2016 in TW Application No. 101134960.
Office Action dated Mar. 14, 2016 in CN Application No. 201280058496 (English translation only).
Zhuang et al, "Polyfluorene-Based Push-Pull Type Functional materials for Write-Once-Read-Many-Times Memory Devices," Chemistry of Materials, vol. 22, No. 15, pp. 4455-4461 (Jul. 16, 2010).
Office Action dated Dec. 4, 2017 in CN Application 201280058496.7.
Office Action dated Jan. 4, 2018 in CN Application No. 201280058424.2.
Office Action dated Nov. 20, 2017 in Ep Application No. 12766430.8.
Office Action dated Apr. 2, 2018 in CN Application No. 201280058424.2.
Office Action dated Dec. 3, 2018 in CN Application No. 201710012220.X.
Office Action dated Sep. 7, 2018 in KR Application No. 10-2014-7010830.
Office Action dated Sep. 28, 2018 in CN Application No. 201280058496.7.
Office Action dated Jul. 19, 2018 in U.S. Appl. No. 14/347,666, by Bascour.
Office Action dated Aug. 3, 2018 in U.S. Appl. No. 14/347,665 by Bascour.
Office Action dated Mar. 14, 2019 in CN Patent Application No. 201280058496.7.
Office Action dated Jan. 10, 2020 in U.S. Appl. No. 14/437,666, by Bascour.
Office Action dated Jan. 28, 2019 in U.S. Appl. No. 14/347,666 by Bascour.
Office Action dated Mar. 1, 2019 in U.S. Appl. No. 14/347,665 by Bascour.
Office Action dated Jun. 5, 2019 in KR Application No. 1020147010829.
Office Action dated Jun. 5, 2019 in KR Application No. 1020147010832.

\* cited by examiner

SPIROBIFLUORENE COMPOUNDS FOR LIGHT EMITTING DEVICES

This application is a U.S. national phase entry under 35 U.S.C. § 371 of International Application No. PCT/EP2012/068809, filed on Sep. 24, 2012, which claims priority to European Application No. 11007868.0, filed on Sep. 28, 2011, and European Application No. 12005988.6, filed Aug. 22, 2012, the entirety of all of which is being incorporated herein by reference for all purposes.

The present invention relates to compounds based on spirobifluorene and light emitting devices comprising said compounds.

Various organic light emitting devices have been under active study and development, particularly those based on electroluminescence (EL) from small organic materials. For such organic devices, the ability to form morphologically stable amorphous films is a key requirement for the development of small materials for organic light emitting diodes (OLEDs). That is because when a small molecule compound is used in the organic light-emitting layer, crystallization usually occurs if the molecule of the compound is too small and its structure is too symmetrical. Therefore, when applied in an organic emission layer, the small molecule compound is vulnerable to morphological change such as crystallization, and once the crystal is formed, it yields negative impacts upon the light-emitting nature and service life of the OLED.

Thermal stress during device operation can lead to such phase transitions from the amorphous state to the thermodynamically stable polycrystalline state leading to dramatic degradation of the device. As a result it is crucial to design materials featuring high glass transition temperature (Tg>150° C.) in order to stabilize the amorphous state. For improving the stability of devices in order to increase operational lifetime, several host materials have been reported. Especially, designing materials having a spiro linkage has been a very successful strategy to obtain OLEDs materials with enhanced morphological stability while keeping their electro-optical functionality.

US2006/0141287 discloses light-emitting layers which include a solid organic material containing a mixture of at least two components. The first host component is an organic compound capable of transporting electrical charges and also forms an aggregate. The second component of the mixture is an organic compound capable of transporting electrical charges and, upon mixing with the first host component, is capable of forming a continuous and substantially pin-hole-free layer. In the reference, as the second component, various compounds such as substituted fluorene derivatives, and spirobifluorene derivatives, etc. are used.

Spirobifluorene, as used herein denotes a structural element of formula (1) and is referred to as SBF hereinafter, whereas Open SBF denotes a system of formula (2) below.

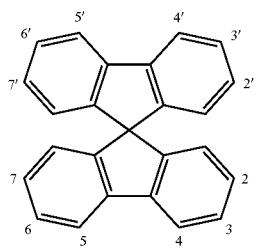

(1)

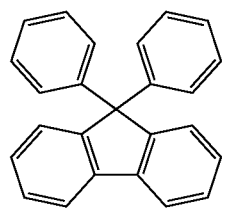

(2)

Substituted spirobifluorene compounds have been extensively described in the prior art, in particular with a substitution of the SBF ring system in "para-position (i.e. the 2, 7, 2' or 7' position of the SBF) by a heteroatom.

Substituted spirobifluorene of this type where the heteroatom bound to the spirobifluorene unit is part of a ring system have also been described.

Salbeck et al., Chem. Rev. 2007, 107, 1011-1065 provides a good overview of spiro compounds useful in organic optoelectronics. Thus, compounds (16) and (17) in Salbeck are the following

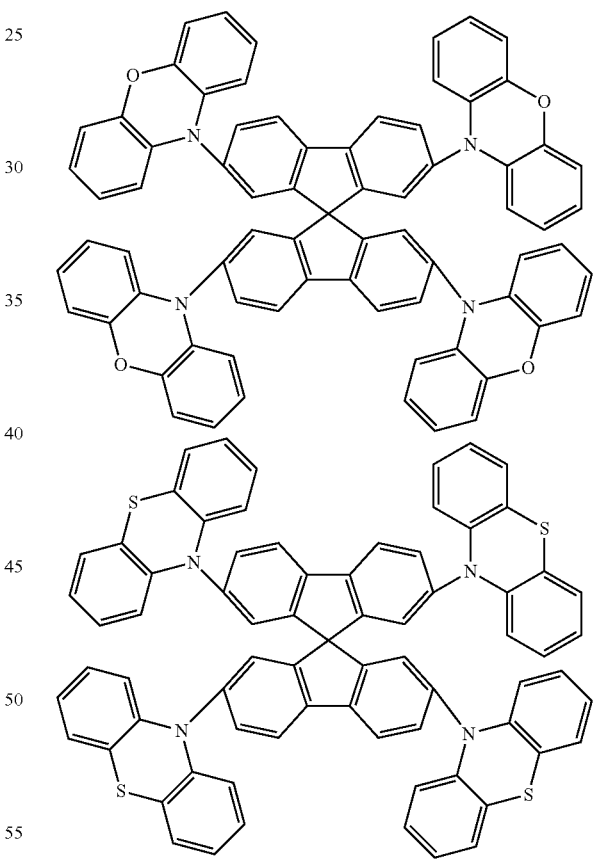

These compounds are reported to have absorption maxima below 400 nm and emission maxima of 491 and 511 nm, respectively. No data on efficiency are given.

BRIEF DESCRIPTION OF DRAWING

A multilayer structure OLED according to one embodiment of the disclosure is depicted in FIG. 1.

Salbeck further reports that replacement of diphenylamino substituents like in the compounds above by carbazole ligands results in a distinct hypsochromic shift of absorption and emission. As an example the compound where the substituents are replaced by N-carbazole shows an absorption maximum below 350 nm and an emission maximum at 372 nm.

Figure 1:
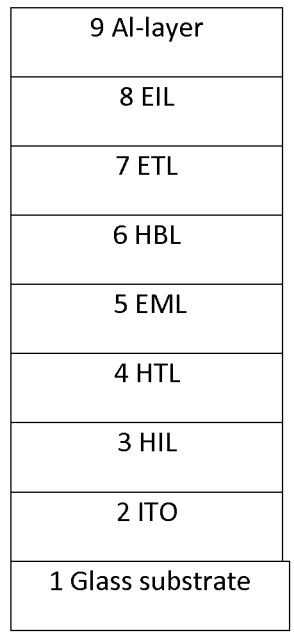

Spirobifluorene compounds with diphenylamino substituents in para-position of the SBF unit are again disclosed in Salbeck et al., see e.g. compounds 42 to 48 thereof.

WO 2011/06574 discloses 4 and 4,4' diphenylamino-substituted SBF compounds (which may be referred to as ortho-substituted compounds relative to the direct bond linking the phenyl rings of the SBF unit).

European Patent Application 2 312 667 discloses compositions for organic electroluminescence elements comprising at least two different materials fulfilling a certain mathematical equation related to the solubility of the materials. Among an extended list of suitable materials having as a common structural feature substituted diphenylamino groups, 3,6-Bis-N,N'-di(4-tert.butylphenyl)amino-spirobifluorene as well as the respective Open SBF derivative are mentioned.

None of the above-disclosed materials meets all the requirements necessary for OLED application, particularly suitable energy level for high phosphorescent efficiency (high triplet energy), high morphological stability, while maintaining other electro-optic and processing properties under operational conditions of the device, such as emission color, dimensional stability, etc, in a fully satisfactory manner. Thus, there has been a need to develop new host materials, which are capable of satisfying all of the requirements indicated above.

Surprisingly, it has been found that spirobifluorene compounds as defined in claim 1 possess a property spectrum which makes them particularly suitable for use in organic electroluminescent devices.

Preferred compounds in accordance with the instant invention are described in the dependent claims and the detailed specification hereinafter.

The compounds of the present invention are characterized by formulae 1 to 12 below

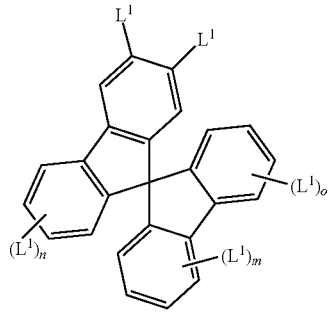
(1)

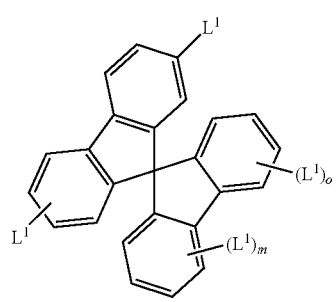
(2)

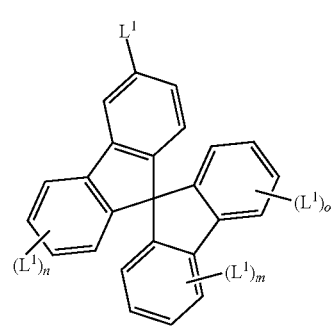

(3)
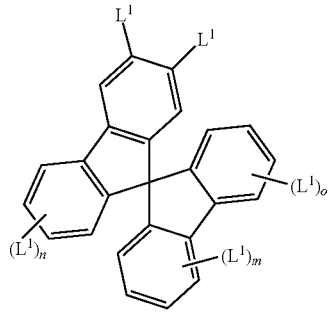

(4)
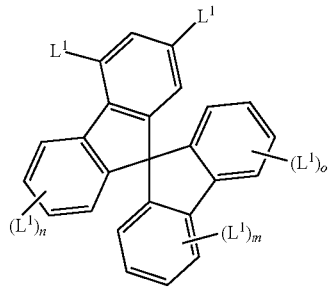

(5)
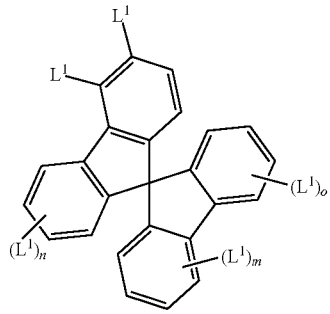

(6)
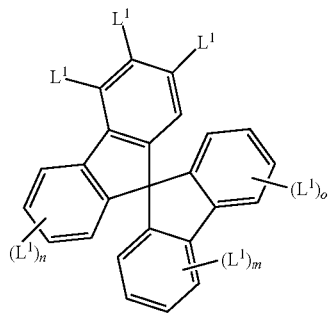

(7)
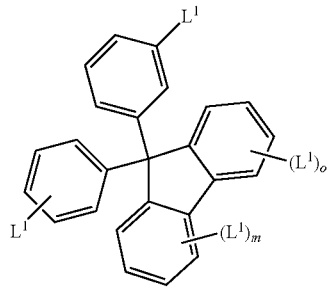

-continued

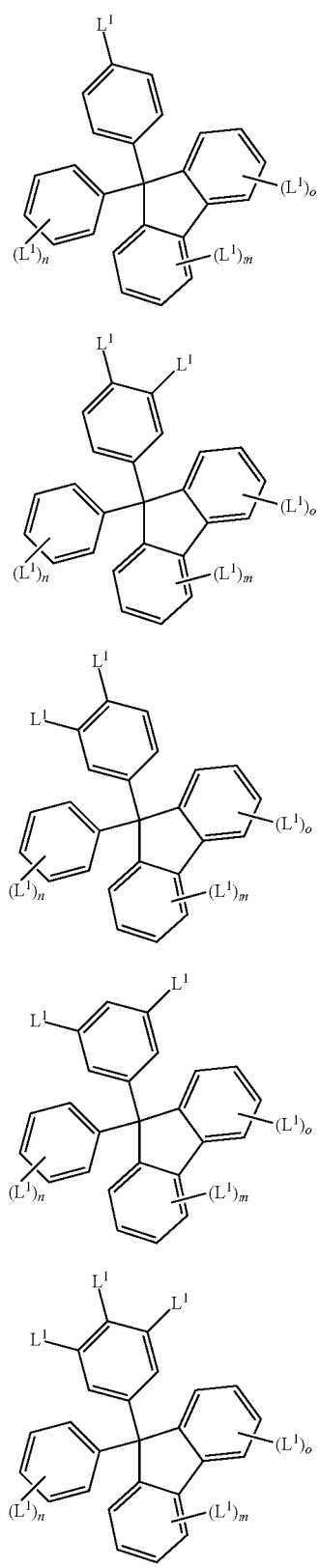

(8)

(9)

(10)

(11)

(12)

wherein n, m and o may be the same or different and represent an integer of from 0 to 3 with the proviso that in compounds of formula 1 at least one of m or o is zero, each of the phenyl rings may carry no ligands other than $L^1$ or may be substituted by ligands other than $L^1$, $L^1$, which may be the same or different in each position, has the formula A

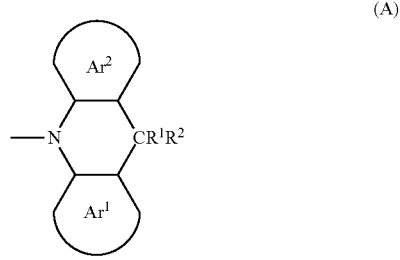

(A)

wherein $R^1$ and $R^2$ may be the same or different in each position and represent hydrogen or an aliphatic group, a carbocyclic group, an aromatic group or a heterocyclic group, all of which may comprise 1 to 20 carbon atoms, and all of which may be substituted or unsubstituted, or a group $OR^3$, a group $NR^4R^5$ or a group $SR^6$, wherein $R^3$ to $R^6$ may be the same or different and represent hydrogen, an alkyl group, a carbocyclic group, an aryl group, a heteroaryl group or a heterocyclic group having 1 to 20 carbon atoms, and $Ar^1$ and $Ar^2$ represent optionally substituted aromatic or heteroaromatic ring systems comprising 4 to 20 ring atoms (the two ring atoms of the heterocyclic ring shown in formula I being part of the aromatic or heteroaromatic ring system for the purpose of counting ring atoms).

For the purpose of the present invention, the term "aliphatic" is intended to denote generally an acyclic hydrocarbon group which may be substituted or unsubstituted and in which the carbon atoms of the main selection can be partly replaced by heteroatoms, which heteroatoms are preferably selected from O, N and S. In a narrower sense, aliphatic group refers to molecules comprising carbon atoms linked in open chains.

The term heteroaryl, for the purpose of the present invention includes monocyclic or polycyclic aromatic ring systems comprising at least one heteroatom, which is preferably selected from nitrogen, oxygen or sulfur, in the ring or at least one of the rings.

In accordance with a first preferred embodiment $R^1$ and $R^2$, which may be the same or different, represent hydrogen, an alkyl group, a carbocyclic group, an aryl group or a heteroaryl group, which groups are substituted or unsubstituted.

In accordance with a second preferred embodiment $R^1$ and $R^2$, which may be the same or different, represent $OR^3$, $NR^4R^5$ or $SR^6$ wherein $R^3$ to $R^6$ have the meaning as defined above.

The compounds in accordance with the present invention share the common feature that the SBF or Open SBF unit is substituted by a nitrogen atom, which is part of a ring system comprising two aromatic or heteroaromatic rings.

The substitution in the SBF system may be para, meta or ortho to the bond linking the phenyl rings in the SBF unit or in the analogous positions of the Open SBF unit.

It has been found that for certain purposes compounds having at least one substituent $L^1$ in meta position can be advantageous in terms of efficiency when used in organic electronic devices.

A first preferred group of compounds are those where $L^1$ has the formula A 1

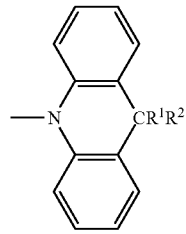
(A-1)

where $R^1$ and $R^2$ are as defined above.

If $R^1$ or $R^2$ represents an alkyl group, same has preferably 1 to 20, especially 1 to 8 carbon atoms and may be straight chain or branched. Particularly preferred alkyl groups are $C_1$ to $C_4$ alkyl like methyl, ethyl, i- or n-propyl and i-, n- and t-butyl. The alkyl groups may themselves be substituted or unsubstituted.

Preferred carbocyclic groups for $R^1$ and $R^2$ are 5 to 7 membered carbocyclic ring systems, which may be saturated or unsaturated like e.g. cyclopentane, cyclohexane or cyclohexene, to give only three examples. As for the alkyl groups, the carbocyclic groups may be substituted or unsubstituted.

Preferred aryl groups for $R^1$ and $R^2$ are phenyl, napththyl, anthracenyl, biphenyl or terphenyl, which may be unsubstituted or substituted by substituents selected from the group consisting of halogen, alkyl, alkoxy, amino, cyano, alkenyl, alkynyl, arylalkyl, aryl and heteroaryl groups or the aryl group may be part of an annealed ring system.

Especially preferred aryl substituents are derived from the following substituted or unsubstituted aryl systems

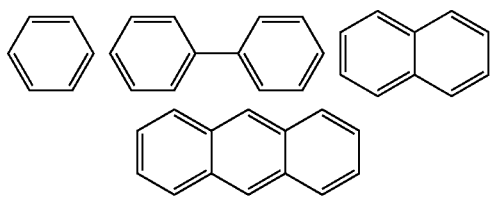

of which phenyl and biphenyl are especially preferred.

A particularly preferred group of heteroaryl groups for $R^1$ and $R^2$ are the following:

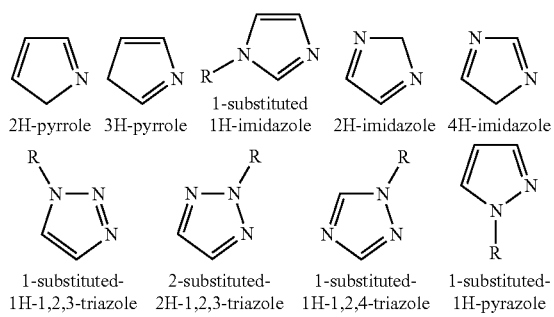

2H-pyrrole  3H-pyrrole  1-substituted 1H-imidazole  2H-imidazole  4H-imidazole 1-substituted- 1H-1,2,3-triazole  2-substituted- 2H-1,2,3-triazole  1-substituted- 1H-1,2,4-triazole  1-substituted- 1H-pyrazole

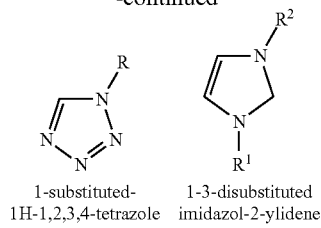

1-substituted- 1H-1,2,3,4-tetrazole    1-3-disubstituted imidazol-2-ylidene

In all these ring systems one or more of the nitrogen atoms may be replaced by another heteroatom like O or S, to name only two examples as shown below:

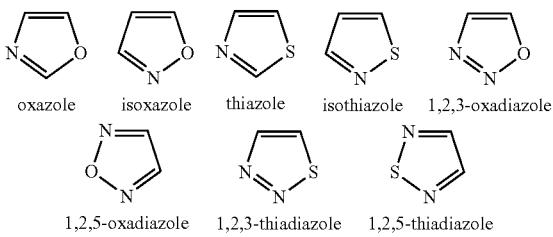

oxazole   isoxazole   thiazole   isothiazole   1,2,3-oxadiazole 1,2,5-oxadiazole   1,2,3-thiadiazole   1,2,5-thiadiazole Still another preferred group of heteroaryl substituents comprises the 6-membered ring systems shown below:

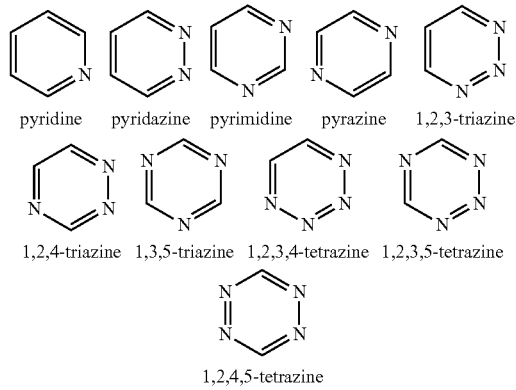

pyridine   pyridazine   pyrimidine   pyrazine   1,2,3-triazine 1,2,4-triazine   1,3,5-triazine   1,2,3,4-tetrazine   1,2,3,5-tetrazine 1,2,4,5-tetrazine The heteroaryl groups may form or be part of an annealed ring system where several rings are condensed or annealed.

The optional substituents of the aforementioned aliphatic, carbocyclic, aromatic or heterocyclic groups, are preferably selected from aliphatic groups, carbocyclic groups, aromatic groups or heterocyclic groups, oxo, $OR^7$, $NR^8R^9$ and $SR^{10}$ groups, wherein $R^7$ to $R^{10}$ are the same or different and represent hydrogen, an aliphatic group, a carbocyclic group, an aromatic group or a heterocyclic group having 1 to 20 carbon atoms.

In accordance with still another preferred embodiment, the substituents of the aliphatic, carbocyclic, aromatic or heteroaromatic groups are selected from the group consisting of halogen, alkyl, alkoxy, aryloxy, oxo, amino, substituted amino, cyano, alkenyl, alkynyl, arylalkyl, aryl and heteroaryl groups, even more preferably from halogen, alkyl, alkoxy, amino, cyano, alkenyl, alkynyl, arylalkyl, aryl and heteroaryl groups.

It is apparent to the skilled person that steric reasons may exclude or render difficult a certain combination of $R^1$ and $R^2$ in the compounds of the present invention, no further explanations n this regard being necessary here.

$Ar^1$ and $Ar^2$, which may be the same or different can be selected from the aromatic or heteroaromatic ring systems described above for substitutents $R^1$ to $R^5$ and thus reference thereto is made at this point. Preferably, $Ar^1$ and or $Ar^2$, which may be the same or different, are aryl ring systems as defined above, preferably phenyl or naphthyl, which may be substituted or unsubstituted.

A further group of preferred compounds in accordance with the present invention are those wherein at least one of n, m or o represents an integer of from 1 to 3.

Also preferred are compounds wherein m and o are both zero.

Further preferred amongst such compounds (where m and o are zero) are compounds of general formula

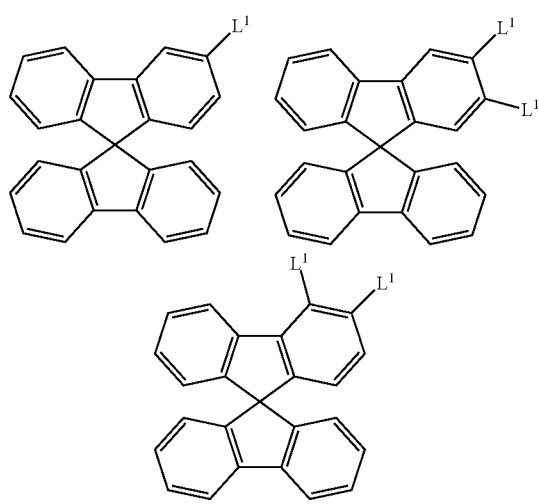

where $L^1$ can have any of the meanings defined above.

The SBF or open SBF ring system may or may not comprise further substituents in addition to substituents $L^1$. If present, such additional substituents, which may be the same or different in each position they occur, are generally selected from of halogen, alkyl, alkoxy, amino, cyano, alkenyl, alkynyl, arylalkyl, aryl and heteroaryl groups.

The compounds in accordance with the present invention may be synthesized by any known and suitable method. The skilled person is aware of suitable manufacturing processes.

Generally, the compounds of the present invention with meta-substituents may be prepared by the following general reaction schemes, which show an exemplary way for compounds carrying one or two ligands $L^1$

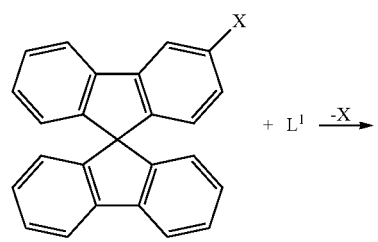

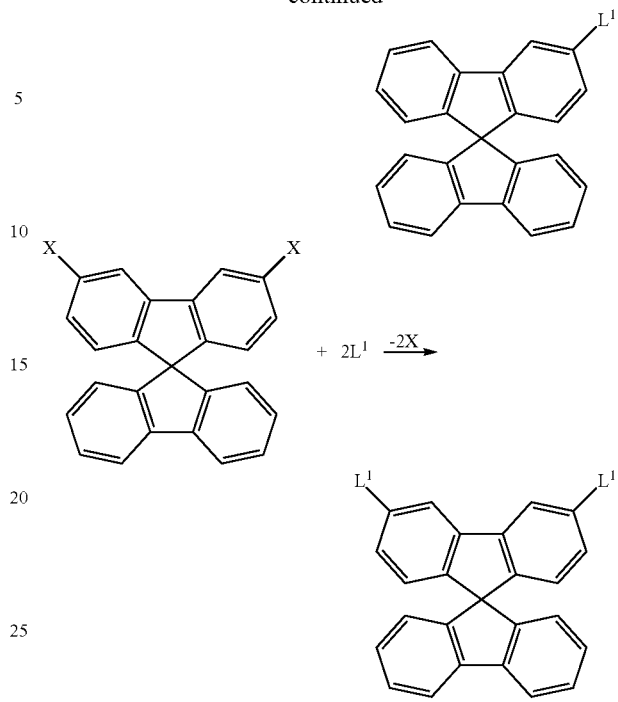

wherein X is a leaving group selected from known leaving groups for such reactions such as halogen, OH, OR, SR, OCN, SCN or CN, especially preferably halogen, in particular chlorine or bromine.

The skilled person will select the suitable reactants and reaction conditions based on the individual needs of a specific synthesis.

The starting materials for such synthesis with at least one leaving group in a meta-position of the SBF or Open SBF ring system may be synthesized in accordance with various process routes which the skilled person will select in accordance with the specific needs. Generally, such compounds are not easily accessible through introduction of the substituents directly into a SBF or Open SBF core as these routes generally yield the para-substituted products preferably due to their higher reactivity. Accordingly, the substituents X have to be introduced through suitable precursor substances e.g. fluorene derivatives, benzophenone derivatives or biphenyl derivatives, to mention only three examples, which are thereafter reacted to yield the SBF or Open SBF structure.

Thus respective compounds may for example be obtained from substituted fluorenone derivatives of formula

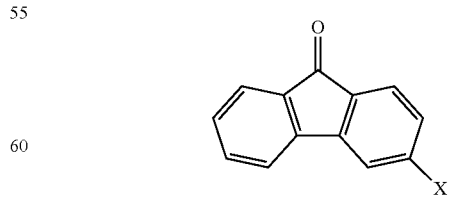

with suitable biphenyl compounds.

Another possibility is the reaction of fluorenones with suitable substituted biphenyl compounds in accordance with the general reaction scheme

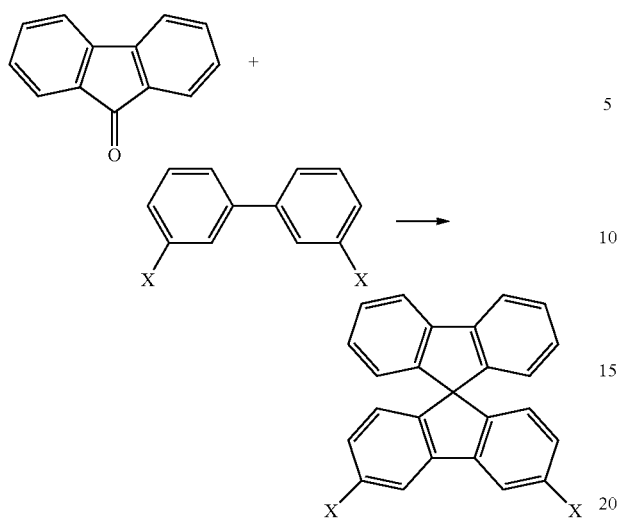

which is described in more detail in JP 2006/089585 for X=OH and which may be adopted for other substituents X.

Another embodiment of the present invention is directed to the use of the compounds of the present invention in an organic light emitting device, especially an organic light emitting diode (OLED).

The compounds in accordance with the present invention may advantageously be used, together with an emitting material, in the emissive layer of an organic light emitting device.

The compounds of the present invention are also suitable as materials for other layers of organic electronic devices.

The present invention is also directed to an organic light emitting device (OLED) comprising an emissive layer (EML), said emissive layer comprising the compounds of the present invention as host material, said host material being notably suitable in an emissive layer (EML) in an OLED.

An OLED generally comprises:

a substrate, for example (but not limited to) glass, plastic, metal;

an anode, generally transparent anode, such as an indium-tin oxide (ITO) anode;

a hole injection layer (HIL) for example (but not limited to) PEDOT/PSS; a hole transporting layer (HTL);

an emissive layer (EML);

an electron transporting layer (ETL);

an electron injection layer (EIL) such as LiF, $Cs_2CO_3$ a cathode, generally a metallic cathode, such as an Al layer.

For a hole conducting emissive layer, one may have a hole blocking layer (HBL) that can also act as an exciton blocking layer between the emissive layer and the electron transporting layer. For an electron conducting emissive layer, one may have an electron blocking layer (EBL) that can also act as an exciton blocking layer between the emissive layer and the hole transporting layer. The emissive layer may be equal to the hole transporting layer (in which case the exciton blocking layer is near or at the anode) or to the electron transporting layer (in which case the exciton blocking layer is near or at the cathode).

The compounds of the present invention may be used preferably used as hosts in an emissive layer.

Optionally, the emissive layer may also contain a polarization molecule, present as a dopant in said host material and having a dipole moment that generally affects the wavelength of light emitted.

A layer formed of an electron transporting material is advantageously used to transport electrons into the emissive layer comprising the light emitting material and the (optional) host material. The electron transporting material may be an electron-transporting matrix selected from the group of metal quinoxolates (e.g. $Alq_3$, Liq), oxadiazoles, triazoles and ketones (e.g. Spirobifluorene ketones SBFK). Examples of electron transporting materials are tris-(8-hydroxyquinoline)aluminum of formula ["$Alq_3$"] and spirobifluorenketone SBFK:

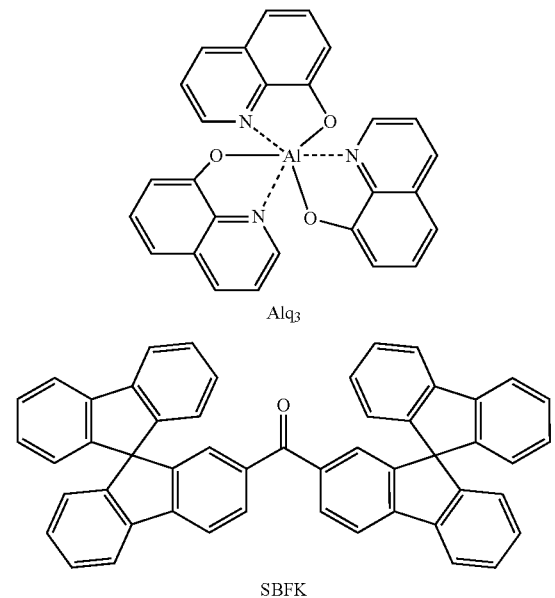

Alq₃

SBFK

A layer formed of a hole transporting material is advantageously used to transport holes into the emissive layer comprising the light emitting material as above described and the (optional) host material. An example of a hole transporting material is 4,4'-bis[N-(1-naphthyl)-N-phenylamino]biphenyl ["α-NPD"].

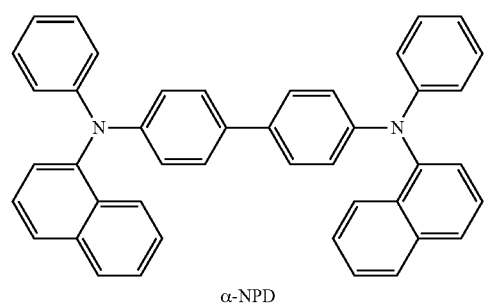 [SMILES: c1ccc(N(c2ccc(-c3ccc(N(c4ccccc4)c4cccc5ccccc45)cc3)cc2)c2cccc3ccccc23)cc1]

α-NPD

The use of an exciton blocking layer ("barrier layer") to confine excitons within the luminescent layer ("luminescent zone") is greatly preferred. For a hole-transporting host, the blocking layer may be placed between the emissive layer and the electron transport layer. An example of a material for such a barrier layer is 2,9-dimethyl-4,7-diphenyl-1,10-phenanthroline (also called bathocuproine or "BCP"), which has the formula

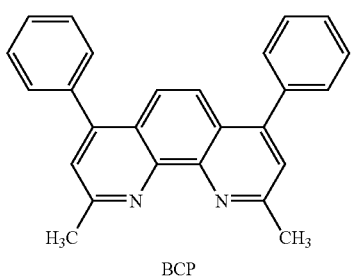

BCP

The OLED has preferably a multilayer structure, as depicted in FIG. 1, wherein 1 is a glass substrate, 2 is an ITO layer, 3 is a HIL layer comprising PEDOT/PSS, 4 is a HTL layer comprising α-NPD, 5 is an EML comprising mCBP as host material and the light emitting material or mixture of these materials as above defined as dopant in an amount of about 15% wt with respect to the total weight of host plus dopant; 6 is a HBL comprising BCP; 7 is an ETL comprising Alga; 8 is an EIL comprising LiF and 9 is an Al layer cathode.

Examples of the present invention are reported hereinafter, whose purpose is merely illustrative but not limitative of the scope of the invention itself.

EXAMPLE 1

Synthesis of 3-Chloro-SBF

Step 1: Synthesis of 1-Bromo-7-chloro-biphenyl

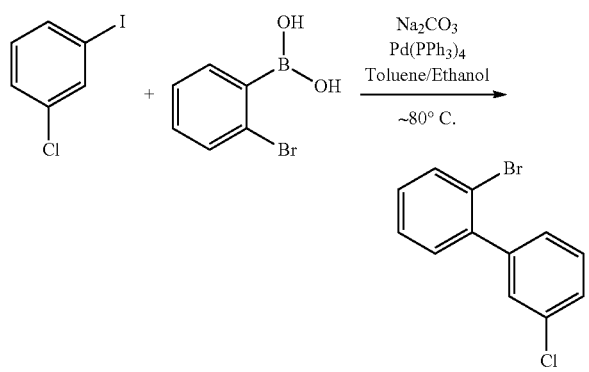

A 50-ml round-bottom flask under nitrogen atmosphere was charged sequentially with Pd(OAc)$_2$ (1.07 g, 0.0047 mol), PPh$_3$ (5.0 g, 0.0032 mol) and dioxane (35 ml). This mixture was added to a 500 ml round bottom flask already filled with 1-Chloro-3-iodobenzene (13.6 g, 0.056 mol) in dioxane (150 ml), 2N aqueous sodium carbonate (180 ml) and 2-Bromophenylboronic acid (12.3 g, 0.059 mol). This mixture was heated at reflux under N$_2$ for 1.5 h and cooled to room temperature. The reaction medium was partitioned between water and ethyl acetate. The combined organic layers were washed with brine, dried over MgSO4, and concentrated. The residue was purified by column chromatography (CH$_2$Cl$_2$/hexane) to afford the desired product with 76.6% yield.

Step 2: 3-chloro-SBF

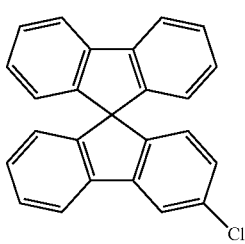 [SMILES: Clc1ccc2c(c1)-c1ccccc1C21c2ccccc2-c2ccccc21]

To a solution of 1-Bromo-7-Chloro-biphenyl (10 g, 0.037 mol) in anhydrous THF (100 ml) cooled to −78° C. a solution of 1.6 M n-BuLi in hexane (0.037 mol, 23.2 ml) was added dropwise. The reaction mixture was stirred at −78° C. for 1 h and a solution of fluorenone (0.031 mol, 5.58 g) in anhydrous THF (25 ml) was added dropwise. After addition, the mixture was allowed to warm to room temperature and stirred for 2 h. The mixture was quenched with saturated NH$_4$Cl (200 ml) and extracted with ethyl acetate (3*125 ml). The combined organic layers were washed with brine, dried over Na$_2$SO4 (or MgSO$_4$) and concentrated in vacuo. The residue was purified by flash chromatography to afford the target compound with ~20% yield.

Step 3—Preparation of 9,9-dimethyl-9,10-dihydroacridine 2-(phenylamino)benzoic acid (50 g, 0.23 mol) was dissolved in methanol (1 L), put in an ice bath and stirred for ten minutes. After slowly adding SOCl$_2$ (60 mL, 0.58 mol) thereto at 0° C., the mixture was stirred under reflux for 12 hours at 90° C. Upon completion of the reaction, the reaction mixture was washed with distilled water and extracted with ethyl acetate. After drying the organic layer with magnesium sulfate and removing the solvent by a rotary type evaporator, 2-(phenylamino) methyl benzoate (47 g, 92%) was obtained through purification by column chromatography using ethyl acetate as developing solvent.

90 g 2-(phenylamino)methyl benzoate (90 g, 0.3 mole) was added to THF (1.5 L) and methyl magnesium bromide (462 mL, 1.38 mole) was slowly added to the mixture, which was thereafter stirred at room temperature for 12 hours. Upon completion of the reaction, the reaction mixture was neutralized with distilled water and extracted with ethyl acetate. After drying the organic layer with magnesium sulfate and removing the solvent by a rotary type evaporator, 80 g (90%) of

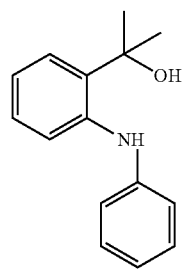 [SMILES: CC(C)(O)c1ccccc1Nc1ccccc1]

was obtained through purification by column chromatography using ethyl acetate as developing solvent 80 g (0.35 mole) of the compound obtained in the previous step was added to 1.7 L of phosphoric acid and the mixture was stirred for 12 hours at room temperature. Upon completion of the reaction, the reaction mixture was neutralized with distilled water and the produced solid was filtered while being washed with water. The solid was dissolved in dichloromethane, extracted and neutralized with sodium hydroxide. After drying the organic layer with magnesium sulfate and removing the solvent by a rotary type evaporator, 64 g 9,9-dimethyl-9,10-dihydroacridine (87%) was obtained via recrystallization in hexane.

3-(9,9-dimethyl-9,10-dihydroacridine)—SBF

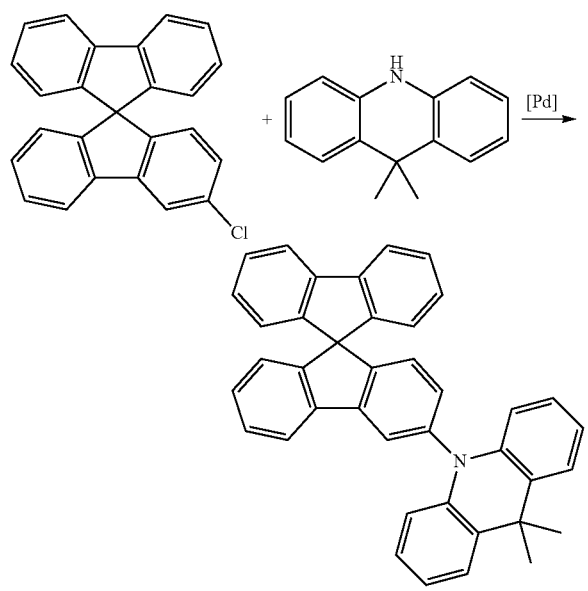

Catalyst Pd(dba)$_2$ (5% mol, 490 mg) and the phosphine P(tBu)$_3$ (4% mol, 0.675 mL of 1M P(tBu)$_3$ in toluene) were introduced at room temperature in toluene (10 mL, anhydrous and well degassed) in a two way flask. After 15 min under nitrogen, the other reagents 3 Cl-SBF (leg, 5.98 g, 16.9 mmol), 9,9-dimethyl-9,10-dihydroacridine (1 eq, 3.53 g, 16.9 mmol) and tBuONa (3 eq, 5.0 g, 60.6 mmol) were introduced and the reaction medium was warmed at 90° C. for 3 hours. At the end of the reaction, the medium was filtrated on diatomaceous earth (celite) and solvent was evaporated under vacuum. The solid was absorbed on silica gel and a dry flash chromatography was realized (methylene chloride/hexane). After solvent evaporation, the solid was recrystallized in hexane (m=7.66 g, yield=87%).

The HOMO level was determined to −5.29 eV, the LUMO level to −1.49 eV and the triplet energy to 2.88 eV.

The HOMO level ($E_{HOMO}$) has been calculated from the half wave potential obtained from the first oxidation ($E_{1ox}^{1/2}$) using the following equation:

$$E_{HOMO}-(-4.8)=-[E_{1ox}^{1/2}-E_{ox}^{1/2}(FC/FC^+)]$$

where $E_{HOMO}$ (ferrocene) has been taken equal to 4.8 eV below the vacuum level.

The E LUMO (CV) have been calculated from the 1st reduction potential.

The triplet energy has been calculated from the highest energy phosphorescence peak in 2-MetTHF (2-methyl tetrahydrofurane) at 77 K.

DEVICE EXAMPLES

All device examples were fabricated by high vacuum thermal evaporation, except for the hole injecting layer which was deposited by spin-coating technique. The anode electrode is 120 nm of indium tin oxide (ITO). All devices were encapsulated with a glass lid sealed with an epoxy resin in a nitrogen glovebox (<1 ppm of H$_2$O and O$_2$) immediately after fabrication, and a moisture getter was incorporated inside the package. The devices were characterized optically and electrically with a C9920-12 External Quantum Efficiency Measurement System from HAMAMATSU. EQE refers to external quantum efficiency expressed in %, while operational stability tests were done by driving the devices at continuous current at room temperature. LT$_{50}$ is a measure of lifetime and corresponds to the time for light output to decrease by 50% of the initial value, when the device is driven at a constant current.

The OLED stack consisted of sequentially, from the ITO surface, 30 nm of Plexcore OC (a self-doping polymer poly(thiophene-3-[2[(2-methoxyethoxy)ethoxy]-2,5-diyl), supplied from Plextronics Inc.) deposited by spin-coating and dried on a hot plate at 200° C. for 20 min. On top of the HIL, 15 nm of NPB were deposited by vacuum-thermal evaporation as hole transporting layer (HTL).

Then a 30 nm layer of Compound B doped with different amounts of dopant Compound C was deposited by vacuum-thermal evaporation as the emissive layer (EML). Then a 5 nm layer of Compound A was deposited by vacuum-thermal evaporation as the hole blocking layer (HBL). Then, a 40 nm layer of Alq3 was deposited by vacuum-thermal evaporation as the electron transporting layer (ETL). The cathode consisted of 1 nm of LiF followed by 100 nm of Aluminum.

As used herein, α-NPD, Compound A, Compound B, Compound C and Alq3 have the following structures

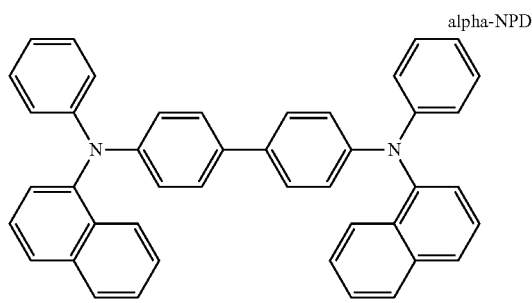

alpha-NPD

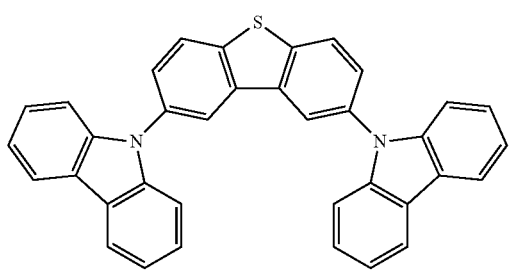

Compound A

-continued

Compound B

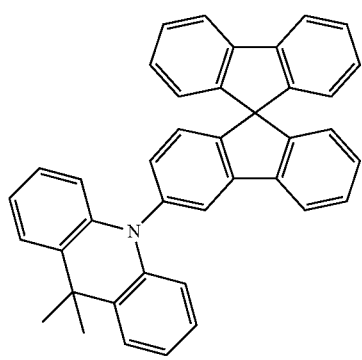

Compound C

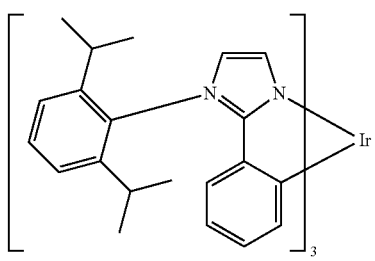

Alq3

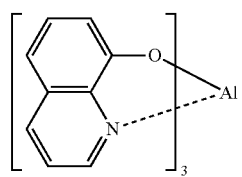

Figure 2:
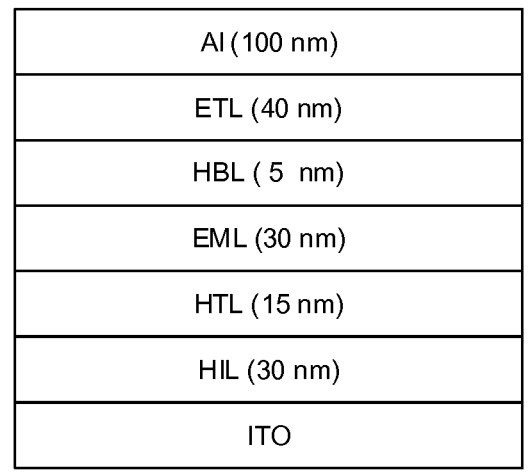

The device structure is summarized in FIG. 2 while Table 1 shows the results measured for the fabricated devices. Compound B was used as host and compound C was used as dopant. The values reported in Table 1 have been measured at a luminance of 1000 Cd/m².

TABLE 1

| Ex. | Dopant % | V | EQE | Lm/W | Cd/A | X | Y | $V_{on}$ | LT50@ 1000 Cd/m2 hrs |
|---|---|---|---|---|---|---|---|---|---|
| 1 | 10 | 7.6 | 8.8 | 9.1 | 22.0 | 0.19 | 0.43 | 3.8 | 64 |
| 2 | 15 | 6.3 | 11.7 | 14.5 | 29.0 | 0.19 | 0.43 | 3.3 | 296 |
| 3 | 20 | 5.6 | 12.0 | 16.8 | 29.9 | 0.19 | 0.43 | 2.9 | 317 |
| 4 | 25 | 5.4 | 12.1 | 17.6 | 30.1 | 0.20 | 0.43 | 3.0 | 66 |
| 5 | 30 | 4.9 | 11.7 | 18.5 | 28.8 | 0.19 | 0.43 | 2.9 | 23 |

As can be seen from the Examples, power efficiency increases with increasing dopant concentration. The lifetime of the devices shows a maximum in the concentration range of from 15 to 20 wt % dopant, relative to the amount of host. Colour coordinates remain nearly constant whereas EQE is lower for 10 Wt % dopant compared to higher concentrations.

The foregoing examples show that the compounds in accordance with the present invention are suitable as host materials in organic light emitting diodes.

The invention claimed is:

1. A compound represented by formula (2):

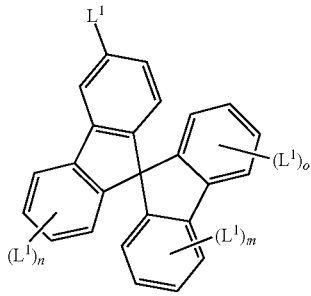

(2)

wherein n, m and o are zero,
each of the phenyl rings may carry no substituents other than $L^1$,
$L^1$ which may be the same or different at each position, has the formula A

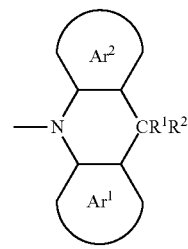

(A)

wherein
$R^1$ and $R^2$ may be the same or different and represent an alkyl group having 1 to 20 carbon atoms,
wherein $R^1$ and $R^2$ are unsubstituted or substituted by substituents selected from the group consisting of halogen, alkyl, alkoxy, aryloxy, oxo, amino, substituted amino, cyano, alkenyl, alkynyl, arylalkyl, aryl and heteroaryl, and $Ar^1$ and $Ar^2$, which may be the same or different, represent optionally substituted aromatic or heteroaromatic ring systems comprising 4 to 20 ring atoms.

2. The compound according to claim 1, wherein $L^1$ has the formula A-1

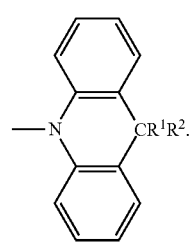

(A-1)

3. The compound according to claim 1 wherein $R^1$ and $R^2$, which may be the same or different, represent an alkyl group having 1 to 20 carbon atoms, which groups are substituted or unsubstituted.

4. The compound according to claim 1 wherein $R^1$ and $R^2$ are unsubstituted or are substituted by substituents selected from the group consisting of halogen, alkyl, alkoxy, amino, cyano, alkenyl, alkynyl, arylalkyl, aryl and heteroaryl.

5. An organic light emitting device comprising a compound according to claim 1.

6. The organic light emitting device of claim 5 wherein the light emitting device is an organic light emitting diode.

7. An emissive layer comprising a host, wherein the host is a compound according to claim 1.

8. An organic light emitting device comprising an emissive layer, said emissive layer comprising a compound according to claim 1 and an emitting material.

9. A compound represented by any of the following formulae (2), (3), (5), (6), (8), (9), (10), and (12):

(2)
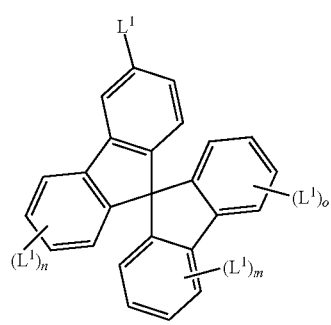

(3)
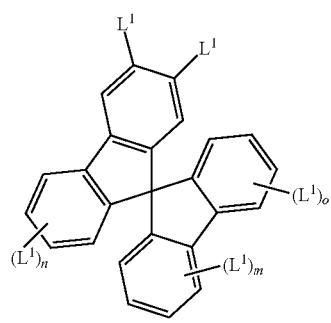

(5)
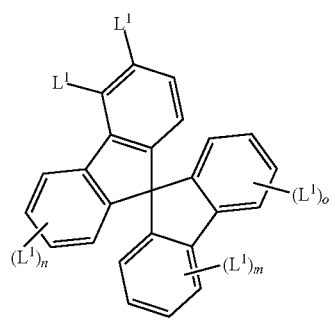

(6)
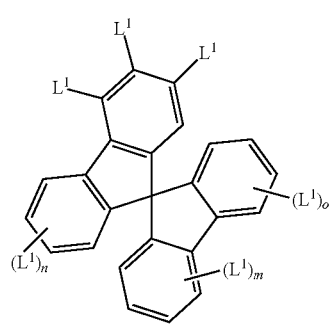

(8)
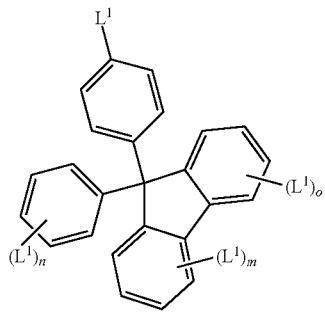

(9)
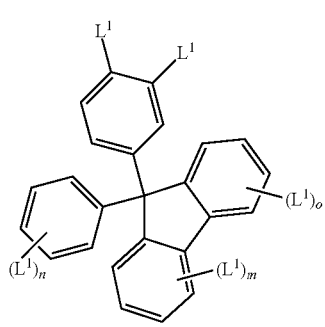

(10)
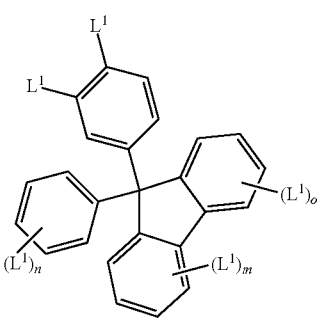

(12)
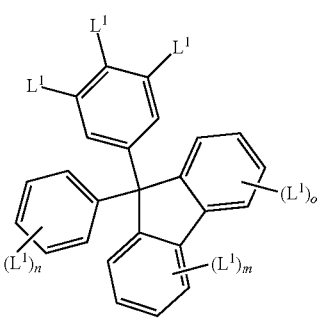

wherein n, m and o are zero, each of the phenyl rings may carry no ligands other than $L^1$ or may be substituted by ligands other than $L^1$, $L^1$ which may be the same or different at each position, has the formula A

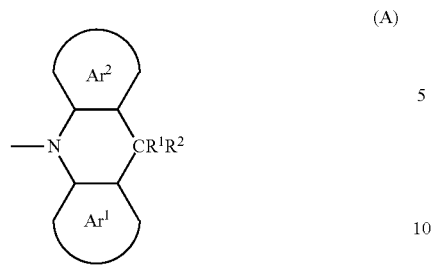

(A)

wherein $R^1$ and $R^2$, which may be the same or different, represent $OR^3$, $NR^4R^5$ or $SR^6$, wherein $R^3$ to $R^6$ represent hydrogen, an aliphatic group, a carbocyclic group, an aryl group, a heteroaryl group or a heterocyclic group having 1 to 20 carbon atoms, and $Ar^1$ and $Ar^2$, which may be the same or different, represent optionally substituted aromatic or heteroaromatic ring systems comprising 4 to 20 ring atoms.

* * * * *